United States Patent
Naidu et al.

(10) Patent No.: US 7,724,866 B2
(45) Date of Patent: May 25, 2010

(54) METHOD OF AND SYSTEM FOR VARIABLE PITCH COMPUTED TOMOGRAPHY SCANNING FOR BAGGAGE SCREENING

(75) Inventors: Ram Naidu, Newton, MA (US); Basak Ulker Karbeyaz, Malden, MA (US); Zhengrong Ying, Wakefield, MA (US); Sergey Simanovsky, Brookline, MA (US); Matthew Hirsch, Somerville, MA (US); David Schafer, Rowley, MA (US); Carl R. Crawford, Brookline, MA (US)

(73) Assignee: Analogic Corporation, Peabody, MA (US)

(*) Notice: Subject to any disclaimer, the term of this patent is extended or adjusted under 35 U.S.C. 154(b) by 504 days.

(21) Appl. No.: 11/769,370

(22) Filed: Jun. 27, 2007

(65) Prior Publication Data

US 2009/0003515 A1 Jan. 1, 2009

(51) Int. Cl.
*A61B 6/03* (2006.01)
(52) U.S. Cl. .............................. 378/15; 378/4; 378/57
(58) Field of Classification Search ............... 378/4–19, 378/57
See application file for complete search history.

(56) References Cited

U.S. PATENT DOCUMENTS

| | | |
|---|---|---|
| 5,473,657 A | 12/1995 | McKenna |
| 5,802,134 A | 9/1998 | Larson et al. |
| 5,881,122 A | 3/1999 | Ruth et al. |
| 5,887,047 A | 3/1999 | Ruth et al. |
| 5,901,198 A | 5/1999 | Ruth et al. |
| 5,909,477 A | 6/1999 | Ruth et al. |
| 5,932,874 A | 8/1999 | Legg et al. |
| 5,937,028 A | 8/1999 | Tybinkowski et al. |
| 5,949,842 A | 9/1999 | Schafer et al. |
| 5,970,113 A | 10/1999 | Crawford et al. |

(Continued)

OTHER PUBLICATIONS

Stierstorfer et al., Segmented multiple plane reconstruction: a novel approximate reconstruction scheme for multi-slice spiral CT, 2002, Physics in Medicine and Biology, vol. 47, pp. 2571-2581.*

(Continued)

*Primary Examiner*—Edward J Glick
*Assistant Examiner*—John M Corbett
(74) *Attorney, Agent, or Firm*—McDermott Will & Emery LLP

(57) ABSTRACT

A method of and a system for variable pitch CT scanning for baggage screening and variable pitch image reconstruction are disclosed. The method comprises decelerating conveyor belt speed when additional time is needed to render a decision on a complex bag; accelerating conveyor belt speed to its normal speed when decisions are reached on undecided bags; generating cone-beam projection data at variable scanning pitch corresponding to variable conveyor belt speed; computing a tilt angle and a distance offset for each tilted slice using the pitch values at which the cone-beam projection data is acquired for that tilted slice; generating fan-beam projection data for each tilted slice using the tilted angle and the distance offset; generating correction projection data to compensate for the error between the source trajectory and the tilted reconstruction plane; generating the corrected fan-beam projection data by adding the correction projection data to the fan-beam projection data; reconstructing tilted slices using the corrected fan-beam projection data; and interpolating the reconstructed tilted slices into axial slices.

11 Claims, 8 Drawing Sheets

U.S. PATENT DOCUMENTS

| | | | |
|---|---|---|---|
| 5,982,843 | A | 11/1999 | Bailey et al. |
| 5,982,844 | A | 11/1999 | Tybinkowski et al. |
| 6,026,143 | A | 2/2000 | Simanovsky et al. |
| 6,026,171 | A | 2/2000 | Hiraoglu et al. |
| 6,035,014 | A | 3/2000 | Hiraoglu et al. |
| 6,067,366 | A | 5/2000 | Simanovsky et al. |
| 6,075,871 | A | 6/2000 | Simanovsky et al. |
| 6,076,400 | A | 6/2000 | Bechwati et al. |
| 6,078,642 | A | 6/2000 | Simanovsky et al. |
| 6,091,795 | A | 7/2000 | Schafer et al. |
| 6,108,396 | A | 8/2000 | Bechwati et al. |
| 6,111,974 | A | 8/2000 | Hiraoglu et al. |
| 6,128,365 | A | 10/2000 | Bechwati et al. |
| 6,195,444 | B1 | 2/2001 | Simanovsky et al. |
| 6,256,404 | B1 | 7/2001 | Gordon et al. |
| 6,272,230 | B1 | 8/2001 | Hiraoglu et al. |
| 6,292,526 | B1 * | 9/2001 | Patch ............ 378/4 |
| 6,317,509 | B1 | 11/2001 | Simanovsky et al. |
| 6,345,113 | B1 | 2/2002 | Crawford et al. |
| 6,442,228 | B1 | 8/2002 | Woloschek et al. |
| 6,687,326 | B1 | 2/2004 | Bechwati et al. |
| 6,721,387 | B1 | 4/2004 | Naidu et al. |
| 6,748,043 | B1 | 6/2004 | Dobbs |
| 6,813,374 | B1 | 11/2004 | Karimi et al. |
| 6,977,984 | B2 | 12/2005 | Hsieh et al. |
| 7,136,450 | B2 | 11/2006 | Ying et al. |
| 7,136,451 | B2 | 11/2006 | Naidu et al. |
| 7,190,757 | B2 | 3/2007 | Ying et al. |
| 7,197,172 | B1 | 3/2007 | Naidu et al. |
| 7,224,763 | B2 | 5/2007 | Naidu et al. |
| 7,242,749 | B2 * | 7/2007 | Hsieh et al. ......... 378/150 |
| 7,492,860 | B2 * | 2/2009 | Garms et al. ......... 378/57 |
| 2003/0072419 | A1 * | 4/2003 | Bruder et al. ......... 378/210 |
| 2005/0238232 | A1 | 10/2005 | Ying et al. |
| 2005/0271293 | A1 | 12/2005 | Ying et al. |
| 2005/0276468 | A1 | 12/2005 | Ying et al. |
| 2006/0002585 | A1 | 1/2006 | Larson et al. |
| 2006/0029180 | A1 * | 2/2006 | Katsevich ............ 378/4 |
| 2006/0039599 | A1 | 2/2006 | Deykoon et al. |
| 2006/0274066 | A1 | 12/2006 | Ying et al. |
| 2007/0014471 | A1 | 1/2007 | Simanovsky et al. |
| 2007/0014472 | A1 | 1/2007 | Ying et al. |
| 2007/0031036 | A1 | 2/2007 | Naidu et al. |

OTHER PUBLICATIONS

Ye et al., Minimum detection windows, Pi-line existence and uniqueness for helical cone-beam scanning of variable pitch, 2004, Medical Physics, vol. 31, No. 3, pp. 566-572.*

Yu et al., A backprojection-filtration algorithm for nonstandard spiral cone-beam CT with an n-PI-window, 2005, Physics in Medicine and Biology, vol. 50, pp. 2099-2111.*

Zhou et al., Feldkamp-type reconstruction algorithms for spiral cone-beam CT with variable pitch, 2007, Journal of X-ray Science and Technology, vol. 15, pp. 177-196.*

Zou et al., Exact Image Reconstruction in a Helical Cone-beam Scan with a Variable Pitch, 2004, 2004 IEEE Nuclear Science Symposium Conference Record, vol. 7, pp. 4200-4203.*

Zou et al., PI-line-based image reconstruction in helical cone-beam computed tomography with a variable pitch, 2005, Medical Physics, vol. 32, No. 8, pp. 2639-2648.*

Li et al., An Exact reconstruction algorithm in variable pitch helical cone-beam CT when PI-line exists, 2006, Journal of X-ray Science and Technology, vol. 14, pp. 109-118.*

Bai et al., Study of an adaptive bolus chasing CT angiography, 2006, Journal of X-ray Science and Technology, vol. 14, pp. 27-38.*

Hsieh et al., Tilted cone-beam reconstruction with row-wise fan-to-parallel rebinning, 2006, Physics in Medicine and Biology, vol. 51, pp. 5259-5276.*

Kachelries, M., et al; Advanced single-slice rebinning in cone-beam spiral CT, Med. Phys., vol. 27, pp. 754-772, (2000).

Defrise, M., et al.; Improved two-dimensional rebinnin of helical cone-beam computerized tomography data using John's equation, Inverse Problems, vol. 19, pp. S41-S54, (2003).

* cited by examiner

METHOD OF AND SYSTEM FOR VARIABLE PITCH COMPUTED TOMOGRAPHY SCANNING FOR BAGGAGE SCREENING

RELATED APPLICATIONS

This patent application and/or patents are related to the following co-pending U.S. applications and/or issued U.S. patents, of the assignee as the present application, the contents of which are incorporated herein in their entirety by reference:

"Nutating Slice CT Image Reconstruction Apparatus and Method," invented by Gregory L. Larson, et al., U.S. application Ser. No. 08/831,558, filed on Apr. 9, 1997, now U.S. Pat. No. 5,802,134, issued on Sep. 1, 1998;

"Computed Tomography Scanner Drive System and Bearing," invented by Andrew P. Tybinkowski, et al., U.S. application Ser. No. 08/948,930, filed on Oct. 10, 1997, now U.S. Pat. No. 5,982,844, issued on Nov. 9, 1999;

"Air Calibration Scan for Computed Tomography Scanner with Obstructing Objects," invented by David A. Schafer, et al., U.S. application Ser. No. 08/948,937, filed on Oct. 10, 1997, now U.S. Pat. No. 5,949,842, issued on Sep. 7, 1999;

"Computed Tomography Scanning Apparatus and Method With Temperature Compensation for Dark Current Offsets," invented by Christopher C. Ruth, et al., U.S. application Ser. No. 08/948,928, filed on Oct. 10, 1997, now U.S. Pat. No. 5,970,113, issued on Oct. 19, 1999;

"Computed Tomography Scanning Target Detection Using Non-Parallel Slices," invented by Christopher C. Ruth, et al., U.S. application Ser. No. 08/948,491, filed on Oct. 10, 1997, now U.S. Pat. No. 5,909,477, issued on Jun. 1, 1999;

"Computed Tomography Scanning Target Detection Using Target Surface Normals," invented by Christopher C. Ruth, et al., U.S. application Ser. No. 08/948,929, filed on Oct. 10, 1997, now U.S. Pat. No. 5,901,198, issued on May 4, 1999;

"Parallel Processing Architecture for Computed Tomography Scanning System Using Non-Parallel Slices," invented by Christopher C. Ruth, et al., U.S. application Ser. No. 08/948,697, filed on Oct. 10, 1997, U.S. Pat. No. 5,887,047, issued on Mar. 23, 1999;

"Computed Tomography Scanning Apparatus and Method For Generating Parallel Projections Using Non-Parallel Slice Data," invented by Christopher C. Ruth, et al., U.S. application Ser. No. 08/948,492, filed on Oct. 10, 1997, now U.S. Pat. No. 5,881,122, issued on Mar. 9, 1999;

"Computed Tomography Scanning Apparatus and Method Using Adaptive Reconstruction Window," invented by Bernard M. Gordon, et al., U.S. application Ser. No. 08/949,127, filed on Oct. 10, 1997, now U.S. Pat. No. 6,256,404, issued on Jul. 3, 2001;

"Area Detector Array for Computed Tomography Scanning System," invented by David A Schafer, et al., U.S. application Ser. No. 08/948,450, filed on Oct. 10, 1997, now U.S. Pat. No. 6,091,795, issued on Jul. 18, 2000;

"Closed Loop Air Conditioning System for a Computed Tomography Scanner," invented by Eric Bailey, et al., U.S. application Ser. No. 08/948,692, filed on Oct. 10, 1997, now U.S. Pat. No. 5,982,843, issued on Nov. 9, 1999;

"Measurement and Control System for Controlling System Functions as a Function of Rotational Parameters of a Rotating Device," invented by Geoffrey A. Legg, et al., U.S. application Ser. No. 08/948,493, filed on Oct. 10, 1997, now U.S. Pat. No. 5,932,874, issued on Aug. 3, 1999;

"Rotary Energy Shield for Computed Tomography Scanner," invented by Andrew P. Tybinkowski, et al., U.S. application Ser. No. 08/948,698, filed on Oct. 10, 1997, now U.S. Pat. No. 5,937,028, issued on Aug. 10, 1999;

"Apparatus and Method for Detecting Sheet Objects in Computed Tomography Data," invented by Muzaffer Hiraoglu, et al., U.S. application Ser. No. 09/022,189, filed on Feb. 11, 1998, now U.S. Pat. No. 6,111,974, issued on Aug. 29, 2000;

"Apparatus and Method for Eroding Objects in Computed Tomography Data," invented by Sergey Simanovsky, et al., U.S. application Ser. No. 09/021,781, filed on Feb. 11, 1998, now U.S. Pat. No. 6,075,871, issued on Jun. 13, 2000;

"Apparatus and Method for Combining Related Objects in Computed Tomography Data," invented by Ibrahim M. Bechwati, et al., U.S. application Ser. No. 09/022,060, filed on Feb. 11, 1998, now U.S. Pat. No. 6,128,365, issued on Oct. 3, 2000;

"Apparatus and Method for Detecting Sheet Objects in Computed Tomography Data," invented by Sergey Simanovsky, et al., U.S. application Ser. No. 09/022,165, filed on Feb. 11, 1998, now U.S. Pat. No. 6,025,143, issued on Feb. 15, 2000;

"Apparatus and Method for Classifying Objects in Computed Tomography Data Using Density Dependent Mass Thresholds," invented by Ibrahim M. Bechwati, et al., U.S. application Ser. No. 09/021,782, filed on Feb. 11, 1998, now U.S. Pat. No. 6,076,400, issued on Jun. 20, 2000;

"Apparatus and Method for Correcting Object Density in Computed Tomography Data," invented by Ibrahim M. Bechwati, et al., U.S. application Ser. No. 09/022,354, filed on Feb. 11, 1998, now U.S. Pat. No. 6,108,396, issued on Aug. 22, 2000;

"Apparatus and Method for Density Discrimination of Objects in Computed Tomography Data Using Multiple Density Ranges," invented by Sergey Simanovsky, et al., U.S. application Ser. No. 09/021,889, filed on Feb. 11, 1998, now U.S. Pat. No. 6,078,642, issued on Jun. 20, 2000;

"Apparatus and Method for Detection of Liquids in Computed Tomography Data," invented by Muzaffer Hiraoglu, et al., U.S. application Ser. No. 09/022,064, filed on Feb. 11, 1998, now U.S. Pat. No. 6,026,171, issued on Feb. 15, 2000;

"Apparatus and Method for Optimizing Detection of Objects in Computed Tomography Data," invented by Muzaffer Hiraoglu, et al., U.S. application Ser. No. 09/022,062, filed on Feb. 11, 1998, now U.S. Pat. No. 6,272,230, issued on Aug. 7, 2001;

"Multiple-Stage Apparatus and Method for Detecting Objects in Computed Tomography Data," invented by Muzaffer Hiraoglu, et al., U.S. application Ser. No. 09/022,164, filed on Feb. 11, 1998, now U.S. Pat. No. 6,035,014, issued on Mar. 7, 2000;

"Apparatus and Method for Detecting Objects in Computed Tomography Data Using Erosion and Dilation of Objects," invented by Sergey Simanovsky, et al., U.S. application Ser. No. 09/022,204, filed on Feb. 11, 1998, now U.S. Pat. No. 6,067,366, issued on May 23, 2000;

"Apparatus and Method for Classifying Objects in Computed Tomography Data Using Density Dependent Mass Thresholds," invented by Ibrahim M. Bechwati, et al., U.S. application Ser. No. 09/021,782, filed on Feb. 11, 1998, now U.S. Pat. No. 6,076,400, issued on Jun. 20, 2000;

"Apparatus and Method for Detecting Concealed Objects in Computed Tomography Data," invented by Sergey Simanovsky, et al., U.S. application Ser. No. 09/228,380, filed on Jan. 12, 1999, now U.S. Pat. No. 6,195,444, issued on Feb. 27, 2001;

"Apparatus and Method for Optimizing Detection of Objects in Computed Tomography Data," invented by Muzaffer Hiraoglu, et al., U.S. application Ser. No. 09/022,062, filed on Feb. 11, 1998, now U.S. Pat. No. 6,272,230, issued on Aug. 7, 2001;

"Computed Tomography Apparatus and Method for Classifying Objects," invented by Sergey Simanovsky, et al., U.S. application Ser. No. 09/022,059, filed on Feb. 11, 1998, now U.S. Pat. No. 6,317,509, issued on Nov. 23, 2001;

"Apparatus and method for processing object data in computed tomography data using object projections," invented by Carl R. Crawford, et al., U.S. application Ser. No. 09/228,379, filed on Jan. 12, 1999, now U.S. Pat. No. 6,345,113, issued on Feb. 5, 2002;

"Apparatus and method for detecting concealed objects in computed tomography data," invented by Sergey Simanovsky, et al., U.S. application Ser. No. 09/228,380, filed on Jan. 12, 1999, now U.S. Pat. No. 6,195,444, issued on Feb. 27, 2001;

"Method of and system for correcting scatter in a computed tomography scanner," invented by Ibrahim M. Bechwati, et al., U.S. application Ser. No. 10/121,466, filed on Apr. 11, 2002, now U.S. Pat. No. 6,687,326, issued on Feb. 3, 2004;

"Method of and system for reducing metal artifacts in images generated by x-ray scanning devices," invented by Ram Naidu, et al., U.S. application Ser. No. 10/171,116, filed on Jun. 13, 2002, now U.S. Pat. No. 6,721,387, issued on Apr. 13, 2004;

"Method and apparatus for stabilizing the measurement of CT numbers," invented by John M. Dobbs, U.S. application Ser. No. 09/982,192, filed on Oct. 18, 2001, now U.S. Pat. No. 6,748,043, issued on Jun. 8, 2004;

"Method and apparatus for automatic image quality assessment," invented by Seemeen Karimi, et al., U.S. application Ser. No. 09/842,075, filed on Apr. 25, 2001, now U.S. No. 6,813,374, issued on Nov. 2, 2004;

"Decomposition of multi-energy scan projections using multi-step fitting," invented by Ram Naidu, et al., U.S. application Ser. No. 10/611,572, filed on Jul. 1, 2003, now U.S. Pat. No. 7,197,172, issued on Mar. 27, 2007;

"Method of and system for detecting threat objects using computed tomography images," invented by Zhengrong Ying, et al., U.S. application Ser. No. 10/831,909, filed on Apr. 26, 2004;

"Method of and system for computing effective atomic number image in multi-energy computed tomography," invented by Zhengrong Ying, et al., U.S. application Ser. No. 10/850,910, filed on May 21, 2004, now U.S. No. 7,190,757, issued on Mar. 13, 2007;

"Method of and system for adaptive scatter correction in multi-energy computed tomography," invented by Zhengrong Ying, et al., U.S. application Ser. No. 10/853,942, filed on May 26, 2004, now U.S. Pat. No. 7,136,450, issued on Nov. 14, 2006;

"Method of and system for destreaking the photoelectric image in multi-energy computed tomography," invented by Zhengrong Ying, et al., U.S. application Ser. No. 10/860,984, filed on Jun. 4, 2004;

"Method of and system for extracting 3D bag images from continuously reconstructed 2D image slices in computed tomography," invented by Zhengrong Ying, et al., U.S. application Ser. No. 10/864,619, filed on Jun. 9, 2004;

"Method of and system for sharp object detection using computed tomography images," invented by Gregory L. Larson, et al., U.S. application Ser. No. 10/883,199, filed on Jul. 1, 2004;

"Method of and system for X-ray spectral correction in multi-energy computed tomography," invented by Ram Naidu, et al., U.S. application Ser. No. 10/899,775, filed on Jul. 17, 2004, now U.S. Pat. No. 7,224,763, issued on May 29, 2007;

"Method of and system for detecting anomalies in projection images generated by computed tomography scanners," invented by Anton Deykoon, et al., U.S. application Ser. No. 10/920,635, filed on Aug. 18, 2004;

"Method of and system for stabilizing high voltage power supply voltages in multi-energy computed tomography," invented by Ram Naidu, et al., U.S. application Ser. No. 10/958,713, filed on Oct. 5, 2004, now U.S. Pat. No. 7,136,451, issued on Nov. 14, 2006;

"Method of and system for 3D display of multi-energy computed tomography images," invented by Zhengrong Ying, et al., U.S. application Ser. No. 11/142,216, filed on Jun. 1, 2005;

"Method of and system for classifying objects using local distributions of multi-energy computed tomography images," invented by Zhengrong Ying, et al., U.S. application Ser. No. 11/183,471, filed on Jul. 18, 2005;

"Method of and system for splitting compound objects in multi-energy computed tomography images," invented by Sergey Simanovsky, et al., U.S. application Ser. No. 11/183,378, filed on Jul. 18, 2005; and "Method of and system for classifying objects using histogram segment features in multi-energy computed tomography images," invented by Ram Naidu, et al., U.S. application Ser. No. 11/198,360, filed on Aug. 4, 2005.

FIELD OF THE DISCLOSURE

The present disclosure relates to methods of and systems for performing computed tomography (CT) scans for baggage screening and processing projection data generated by CT scanners, and more particularly to a method of and a system for performing variable pitch scanning for baggage screening and reconstructing images using projection data acquired by variable pitch scanning.

BACKGROUND OF THE DISCLOSURE

Constant pitch helical cone beam (CB) computed tomography (CT) is used for most applications. The pitch is defined as the ratio of the conveyor or table displacement per gantry rotation to the size of the detector array along the direction of conveyor or table movement.

For example, CT based explosive detection systems (EDS) for checked baggage screening use a constant pitch. However in carry-on baggage screening at checkpoint, the distance between the entrance of a bag and the exit of a bag is much shorter than the corresponding distance in checked baggage screening. Screeners may have to stop the conveyor belt from time to time in order to have enough time to resolve complex alarmed bags on screen.

When a line scanner is used for pre-screening followed by a CT scanner in carry-on baggage screening, it is advantageous for the CT scanner to vary the belt speed: when a bag is cleared by the line scanner, the CT scanner speeds up the belt to its maximum speed to carry the bag to the exit of the scanner without further examination; when a bag can not be cleared by the line scanner, the CT scanner returns to its normal speed to scan the bag, reconstruct CT images, and perform threat detection on the bag.

Variable pitch scanning schemes have been proposed in the prior art. Woloschek et al. (U.S. Pat. No. 6,442,228) use additional sensors to obtain dynamic parameters such as the table speed and integrate these parameters into the projection data stream for image reconstruction.

Hsieh et al. (U.S. Pat. No. 6,977,984) use a helical weighting method of reconstructing CT images with projection data acquired at variable pitch. The helical weighting method suffers significant cone beam artifacts for the CT scanners with more than eight rows of detectors. Furthermore, the method does not provide a continuous reconstruction of continuous data acquisition in the baggage screening application.

SUMMARY OF THE DISCLOSURE

The present disclosure provides a method of and a system for variable pitch CT scanning for baggage screening. In accordance with one aspect of the disclosure, the method and system provide for scanning a continuous flow of baggage with the conveyor belt being stopped from time to time. In accordance with the one aspect of the disclosure, the method and system reconstruct projection data acquired at variable pitch due to the change of the belt speed for baggage screening. In accordance with another aspect of the disclosure, the disclosed method and system provide a more convenient, better image quality, and less labor intensive CT baggage screening scheme at checkpoint.

In one embodiment of the present disclosure, a conveyor system comprises a main conveyor belt and an exit conveyor belt. When it takes more than a pre-defined time for operators to make a decision on a complex bag, the main conveyor belt decelerates and stops taking any new bags for scanning, and the exit conveyor belt also stops afterwards. After all the bags on the exit conveyor belt are examined on screen and are transported out of the exit conveyor belt, the main conveyor belt accelerates to its normal speed.

In one embodiment of the present disclosure, an improved image reconstruction method is provided to handle the acceleration and deceleration of the main conveyor belt. The image reconstruction method uses nutating or tilted slices for reconstruction to reduce cone-beam artifacts. The tilt angle for each slice is dynamically calculated based on the belt speed or pitch, which is defined as the ratio of the belt displacement in one gantry rotation to the detector array width along the belt movement direction.

In one embodiment of the present disclosure, the tilt angle is calculated based on the pitch value corresponding to the central projection view angle. Other variations for calculating the tilt angle include, but are not limited to, finding an optimal tilt angle that minimizes the source trajectory error for all the projection view angles within the tilted slice; and low-pass filtering the tilt angles using several consecutive slices to reduce the noise and outlier data points with regards to the belt speed and the belt position.

In another embodiment of the present disclosure, the tilt angle is optimized in combination with a distance offset of the reconstruction plane along the Z-axis of the scanner. The optimal tilt angle and the optimal distance offset of the reconstruction plane are obtained when the mean square error of the x-ray source trajectory and the reconstruction plane is minimized. Other definitions of the error including, but not limited to, absolute of the difference between the x-ray source trajectory and the reconstruction plane can also be used.

In one embodiment of the present disclosure, an intersection curve of the tilted reconstruction plane and the detector plane is calculated, and then fan-beam projection data for the tilted slice is generated from the cone-beam projection data on the intersection curve. Linear interpolation is used along the detector row directions to generate the fan-beam projection data. Other types of interpolation including cubical, bi-linear, and bi-cubical interpolations can also be used.

In one embodiment of the present disclosure, correction projection data is generated from the cone-beam data to compensate for errors between the x-ray source trajectory and tilted reconstruction plane. The generation of the correction projection data comprises generating second order derivatives with respect to the projection angle and the detector column direction; and computing a summation (the discrete form of an integral) of weighted second order derivatives along the detector row direction.

In an alternative embodiment of the present disclosure, the generation of the correction projection data comprises generating first order derivatives with respect to the projection angle and the detector column direction; and computing a summation of weighted first order derivatives only on these perturbed detector positions without summing over the detector row direction.

In one embodiment of the present disclosure, the correction projection data is added to the fan-beam projection data to back-project a tilted image slice. The back-projection of the corrected fan-beam projection data uses filtered back-projection method. Other variations of the back-projection of the corrected fan-beam data include rebinning the corrected fan-beam data into parallel projection data followed by a parallel filtered back-projection.

In an alternative embodiment of the present disclosure, the fan-beam projection data generated from the cone-beam projection data is directly back-projected to a tilted image slice without generating and using the correction projection data.

In one embodiment of the present disclosure, each tilted slice is generated at a fixed distance interval, where the distance interval is measured along the Z-axis of the scanner. In an alternative embodiment of the present disclosure, each tilted slice is generated at a fixed time interval or fixed rotation angle interval.

In one embodiment of the present disclosure, axial slices are generated using linear interpolation among tilted slices on a pixel-by-pixel basis. An axial slice is generated at Z (belt movement direction) positions where tilted slices intersect with the Z-axis at the isocenter. However, axial slices can also be generated at other Z positions. The generation of each pixel of an axial slice comprises finding two closest tilted slices such that the axial pixel resides in the middle of the two corresponding pixels of the two tilted slices, and linearly interpolating these two pixels of the two tilted slices to generate the axial pixel.

A system for variable pitch CT scanning for baggage screening is also disclosed. In various embodiments, the system includes modules configured to implement each of the above-identified functions. The system may include a conveyor system including a main conveyor belt and an exit conveyor belt, belt position sensors, and an image reconstrutor which implements the selected functions of the above described variable pitch image reconstruction methods.

BRIEF DESCRIPTION OF THE DRAWINGS

The drawing figures depict preferred embodiments by way of example, not by way of limitations. In the figures, like reference numerals refer to the same or similar elements.

DETAILED DESCRIPTION OF THE PREFERRED EMBODIMENTS

Figure 1:
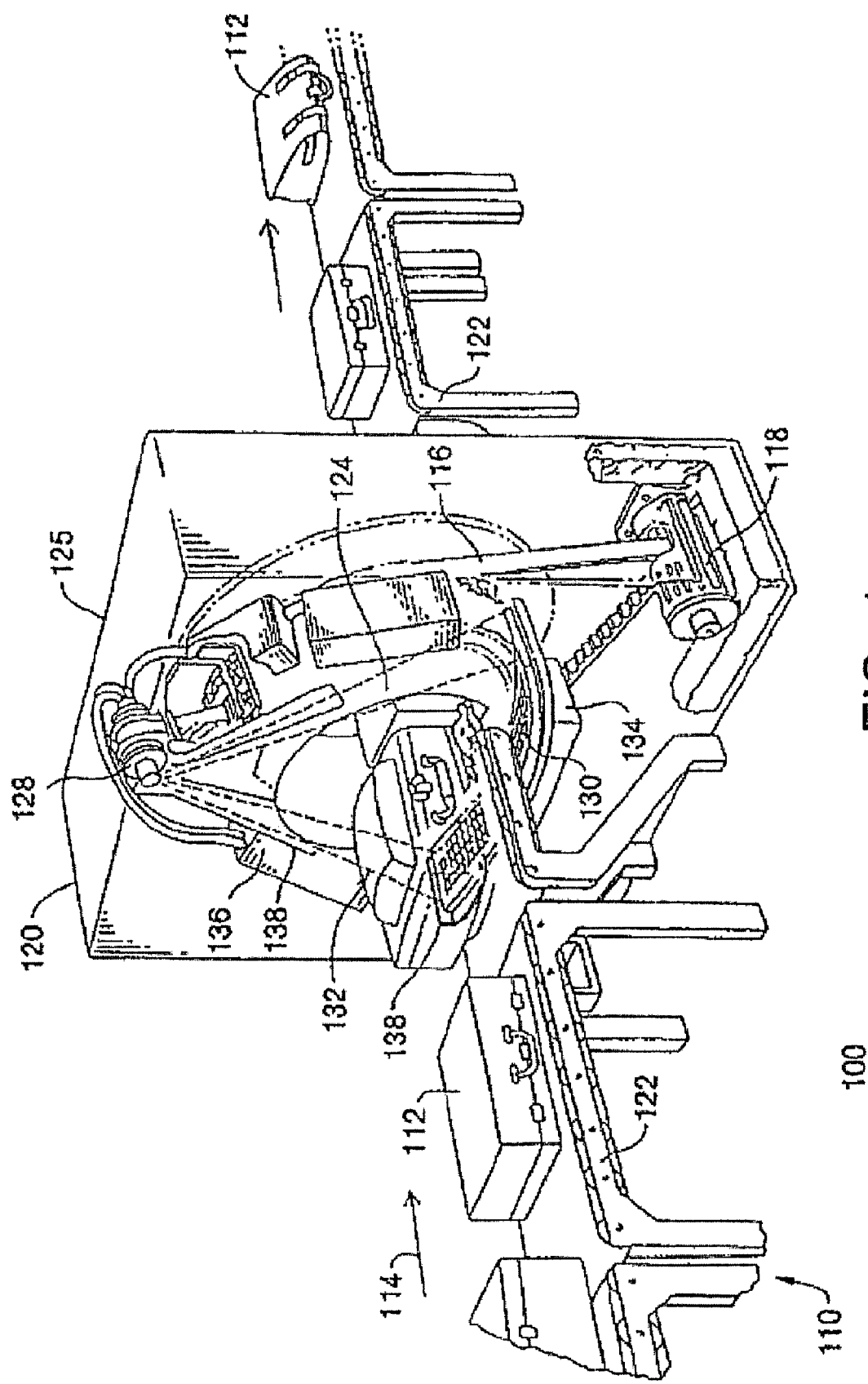
FIG. 1 is a perspective view of a baggage scanning system which can be adapted to embody the system and perform the method described herein.
Figure 2:
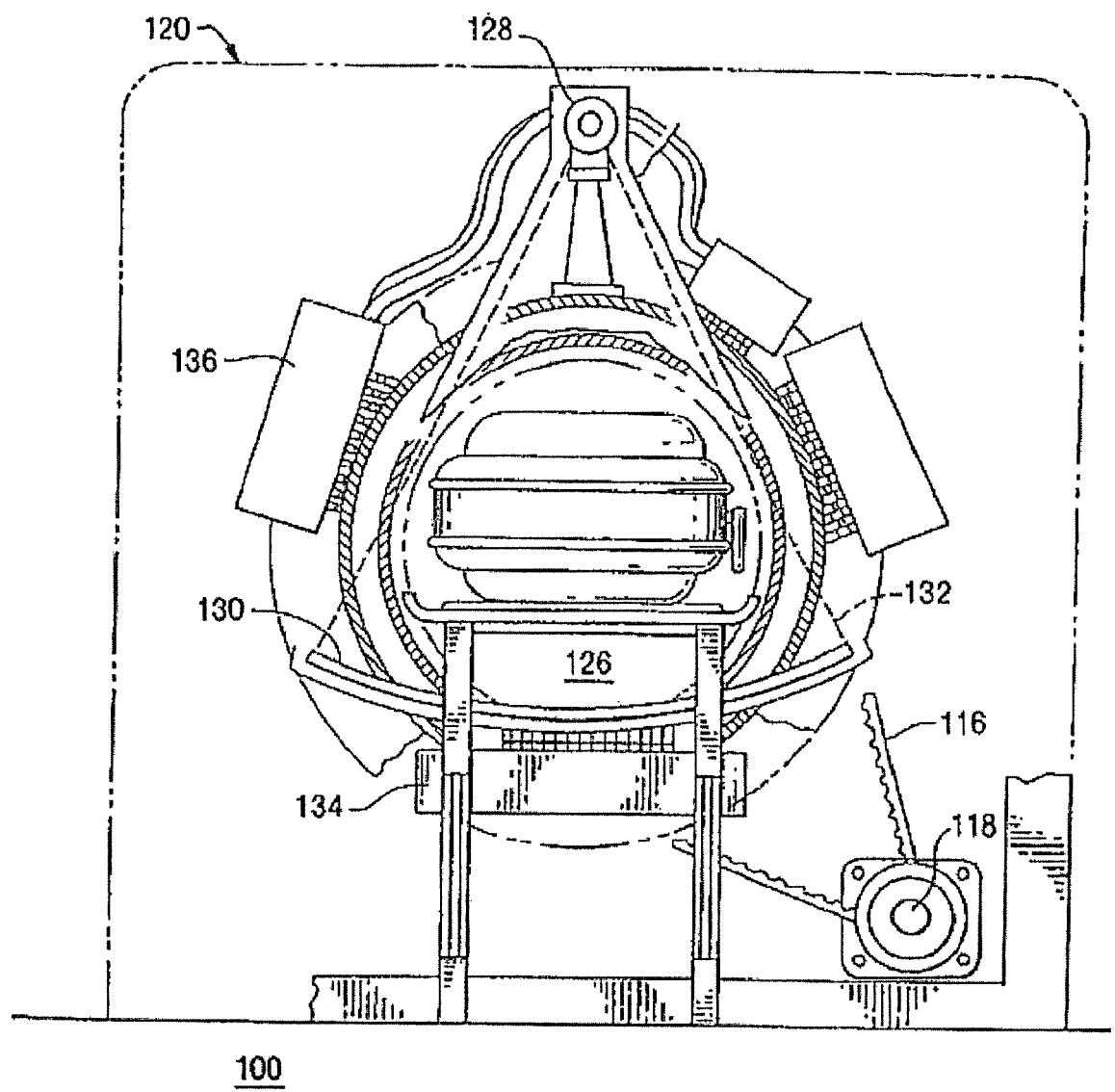
FIG. 2 is a cross-sectional end view of the system of FIG. 1.
Figure 3:
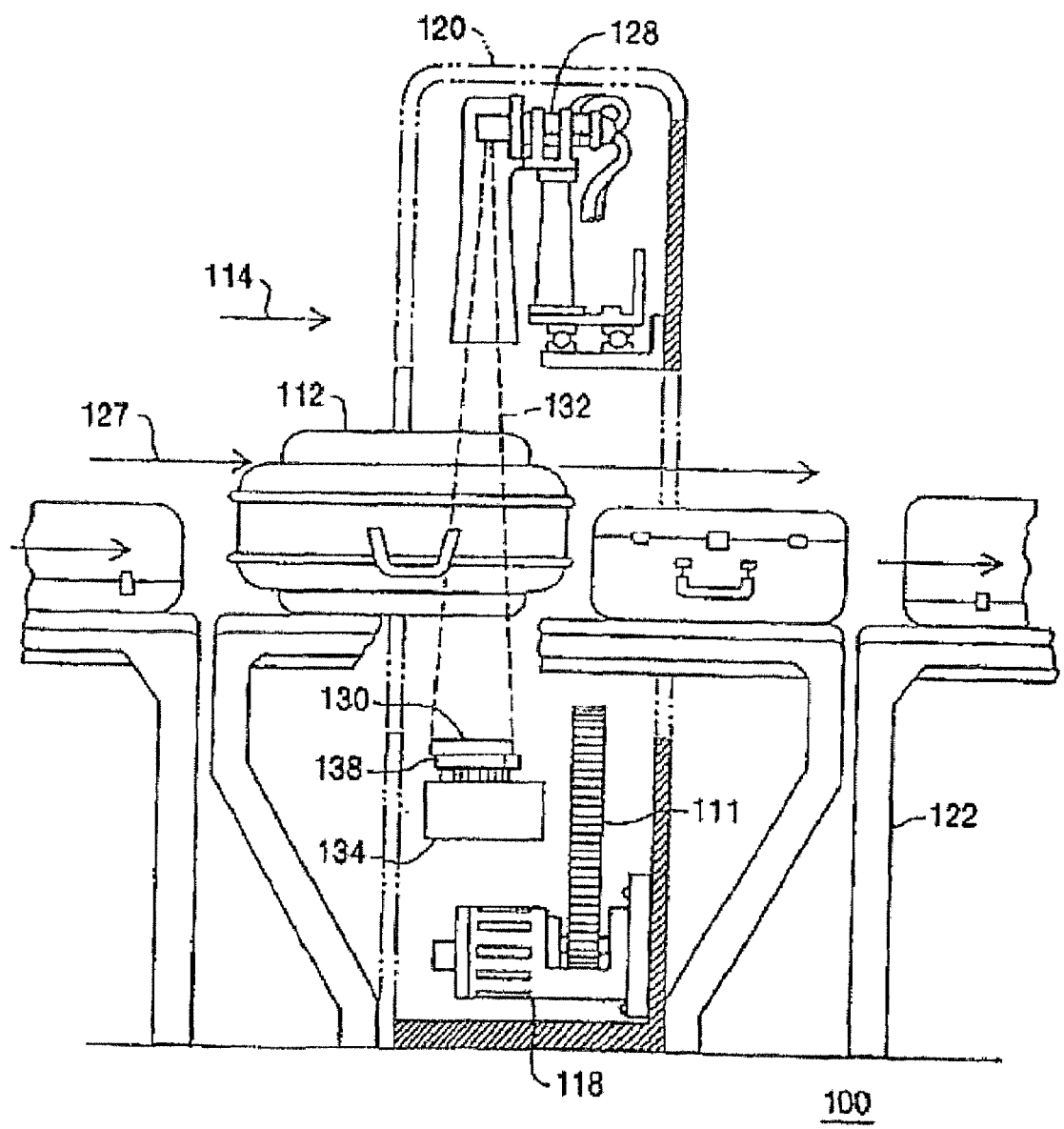
FIG. 3 is a cross-sectional radial view of the system of FIG. 1.

Referring to the drawings, FIGS. 1, 2 and 3 show perspective, end cross-sectional, and radial cross-sectional views, respectively, of a typical baggage scanning system 100, which includes a conveyor system 110 for continuously conveying baggage or luggage 112 in a direction indicated by arrow 114 through a central aperture of a CT scanning system 120. The conveyor system includes motor driven belts for supporting the baggage. Conveyer system 110 is illustrated as including a plurality of individual conveyor sections 122; however, other forms of conveyor systems may be used.

The CT scanning system 120 includes an annular shaped rotating platform, or disk, 124 disposed within a gantry support 125 for rotation about a rotation axis 127 (shown in FIG. 3) that is preferably parallel to the direction of travel 114 of the baggage 112. Disk 124 is driven about rotation axis 127 by any suitable drive mechanism, such as a belt 116 and motor drive system 118, or other suitable drive mechanism, such as the one described in U.S. Pat. No. 5,473,657 issued Dec. 5, 1995 to Gilbert McKenna, entitled "X-ray Tomographic Scanning System," which is assigned to the present assignee and, which is incorporated herein in its entirety by reference. Rotating platform 124 defines a central aperture 126 through which conveyor system 110 transports the baggage 112.

The system 120 includes an X-ray tube 128 and a detector array 130 which are disposed on diametrically opposite sides of the platform 124. The detector array 130 is preferably a two-dimensional array, such as the array described in U.S. Pat. No. 6,091,795 entitled, "Area Detector Array for Computed Tomography Scanning System." Other suitable arrays are known in the art. The system 120 further includes a data acquisition system (DAS) 134 for receiving and processing signals generated by detector array 130, and an X-ray tube control system 136 for supplying power to, and otherwise controlling the operation of, X-ray tube 128. The system 120 is also preferably provided with a computerized system (not shown) for processing the output of the data acquisition system 134 and for generating the necessary signals for operating and controlling the system 120. The computerized system can also include a monitor for displaying information including generated images. System 120 also includes shields 138, which may be fabricated from lead, for example, for preventing radiation from propagating beyond gantry 125.

The X-ray tube 128 may generate a pyramidally-shaped beam, often referred to as a "cone beam," 132 of X-rays that pass through a three dimensional imaging field, through which conveying system 110 transports baggage 112. After passing through the baggage disposed in the imaging field, detector array 130 receives cone beam 132 and generates signals representative of the densities of exposed portions of baggage 112. The beam therefore defines a scanning volume of space. Platform 124 rotates about its rotation axis 127, thereby transporting X-ray source 128 and detector array 130 in circular trajectories about baggage 112 as the conveyor system 110 continuously transports baggage through central aperture 126, so as to generate a plurality of projections at a corresponding plurality of projection angles. When dual energy scanning mode is configured, the control system 136 supplies modulated high voltages with respect to alternating projection angles to the X-ray tube 128. The detector array 130 then receives data corresponding to high-energy and low-energy X-ray spectra in alternating projection angles.

Figure 4A:
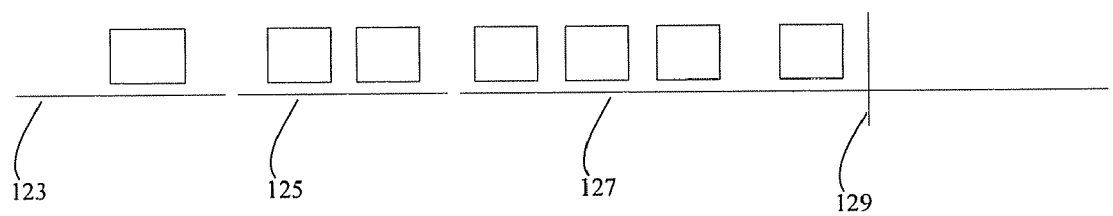
FIG. 4A is an illustration of an embodiment of a three-section conveyor belt system with constant pitch scanning.

In the baggage screening application at checkpoint, operators may not be able to keep up with the bag throughput at a peak time. FIG. 4A illustrates by way of example a three-section conveyor system 110, which comprises three conveyor belts: an entrance conveyor belt 123, a main conveyor belt 125, and an exit conveyor belt 127. Operators perform on-screen threat resolution for each scanned bag. The on-screen threat resolution includes resolving threats detected by automatic explosive and weapon detection algorithms and visually identifying prohibited items. For a complex bag, it may take more than the average time for operators to make a decision, and the conveyor system 110 has to be able to handle such a case.

When operators spend more than a pre-defined response time, at which an undecided bag travels to the position 129 at the exit conveyor belt 127, the entrance conveyor belt 123 stops taking any bags to the main conveyor belt. The exit conveyor belt 127 stops also after all the bags inside the main conveyor belt 125 are transported to the exit conveyor belt. Therefore, the portion of the exit conveyor belt from the position 129 to the end of the exit conveyor belt should be at least the same length as the main conveyor belt. After the entrance and exit conveyor belts decelerate and are stopped, operators can take as much time as necessary to examine all the bags on the exit conveyor belt. After the operators finish inspecting all the bags on the exit conveyor belt, the exit conveyor belt resumes by accelerating until it reaches its normal speed; with the entrance conveyor belt also resuming by accelerating until it reaches its normal speed. The baggage screening system thus returns to its normal operation mode. During the above transitional time, the main conveyor belt remains at a constant speed; therefore the CT scanner acquires projection data at a constant pitch.

Figure 4B:
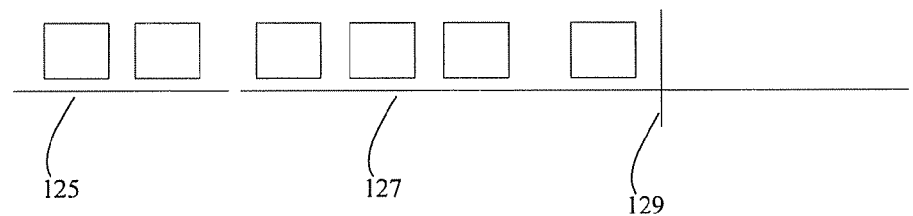
FIG. 4B is an illustration of an embodiment of a two-section conveyor belt system with variable pitch scanning.

However, some airports may not have space to hold an entrance conveyor belt or a long exit conveyor belt such as a three-section conveyor belt, and instead uses, for example a two-section conveyor belt. FIG. 4B illustrates an example of a two-section conveyor system. In the two-section conveyor system, the main conveyor belt 125 has to perform the function of the entrance conveyor belt, that is, the main conveyor belt has to decelerate to a stop when operators take more than a pre-defined response time to make a decision. The exit conveyor belt can be shorter than the exit conveyor belt of a three-section conveyor system. The average response time limit position 129 can be at the end of the exit conveyor belt. After the main conveyor belt stops, typically the exit conveyor belt then decelerates to a stop. Operators now can take as much time as necessary to examine the bag. After all the bags on the exit conveyor belt have been examined on screen, the main conveyor belt resumes and accelerates to its normal speed. During the stop and start of the main conveyor belt, as the main conveyor belt is decelerating and accelerating, respectively, the CT scanner acquires projection data at a variable pitch, which requires performing variable pitch image reconstruction.

Figure 5A:
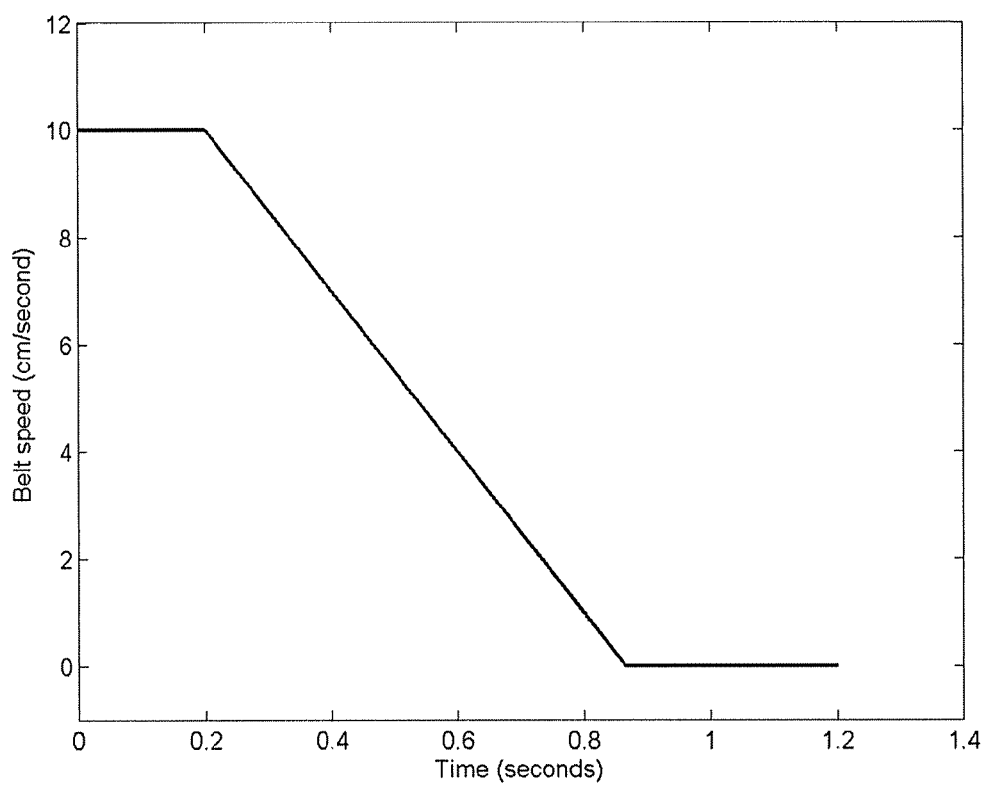
FIG. 5A is a plot of an example of the speed profile when the belt decelerates.
Figure 5B:
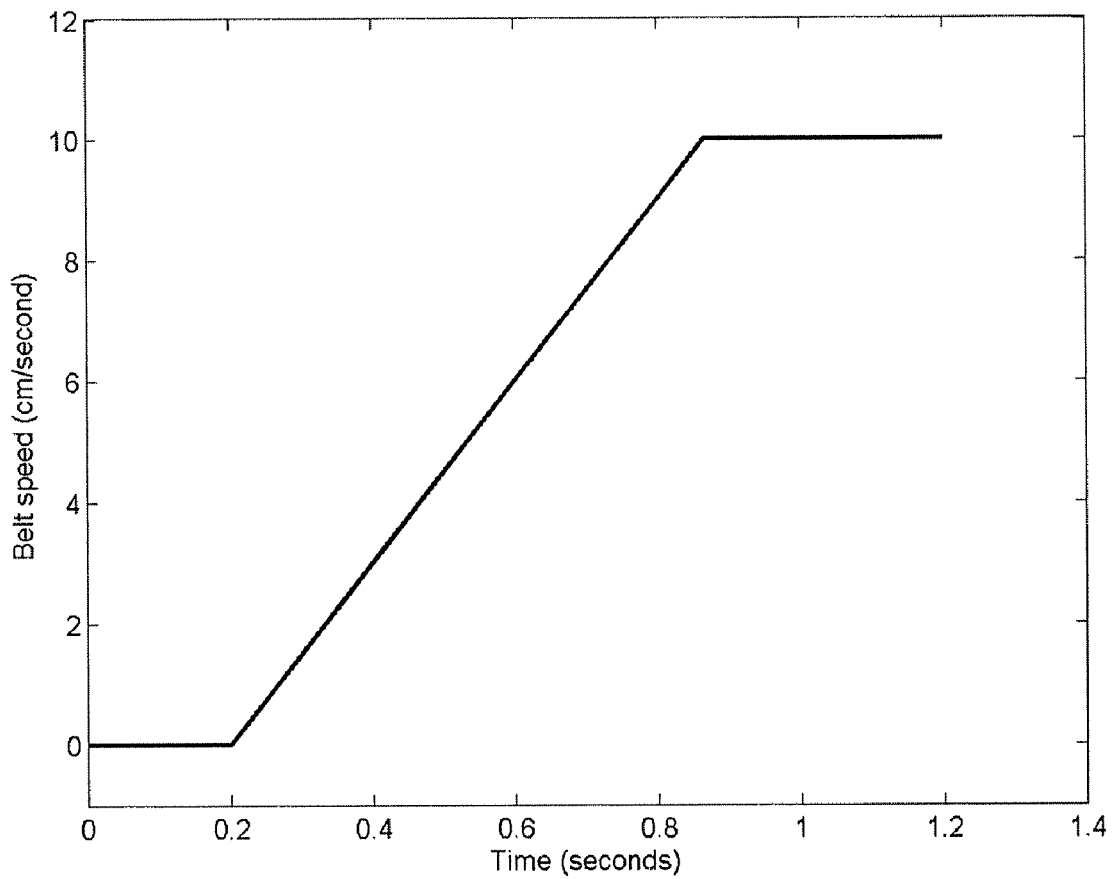
FIG. 5B is a plot of an example of the speed profile when the belt accelerates.

It is desirable to decelerate (accelerate) the belt as fast as possible, however due to the physical limits of the system, a typical deceleration (acceleration) of the belt is to stop (start) the belt from (to) its normal speed (e.g., a typical normal speed is 10 centimeters per second, although the speed that is considered normal can clearly vary) within one gantry rotation time (e.g., a typical time interval for one gantry rotation is 0.67 seconds, although this can clearly vary also). FIG. 5A shows an example of a belt speed profile of a belt decelerating from 10 cm/second to a complete stop in 0.67 seconds. FIG. 5B shows an example of a belt speed profile of a belt accelerating from a complete stop to 10 cm/second in 0.67 seconds. Note that the gantry rotation speed usually does not change while the belt decelerates or accelerates; however, the disclosed method and system can directly apply to the scenarios where the gantry rotation speed also changes without any modification.

One embodiment of the improved image reconstruction method provided in this disclosure can be implemented as an extension of the tilted or nutated 2D image reconstruction method for reconstructing helical cone beam data as described in "Advanced single-slice rebinning in cone-beam spiral CT," Med. Phys., vol. 27, pp. 754-772, 2000 by M. Kachelriess, S. Schaller, and W. Kalender, (hereinafter referred to as "ASSR Method") and in U.S. Pat. No. 5,802, 134. The advantage of using 2D image reconstruction over 3D cone beam reconstruction is the simplicity of incorporation of the variable pitch into the reconstruction, resulting in a faster and cheaper reconstruction system than using 3D reconstruction. In tilted 2D reconstruction, the reconstruction plane is tilted to better fit the helix of the x-ray source trajectory. The tilt angle is a function of the pitch; therefore variable pitch image reconstruction can be accomplished by varying the tilt angle of the reconstruction plane. In addition to the dynamic calculation of the tilt angle for the tilted reconstruction plane, it is beneficial, although not necessary, to have another adaptation of the reconstruction plane to minimize the error between the source trajectory and the reconstruction plane. The second adaptation of the reconstruction plane is to shift the reconstruction along the Z-axis so that the error is minimized.

Figure 6:
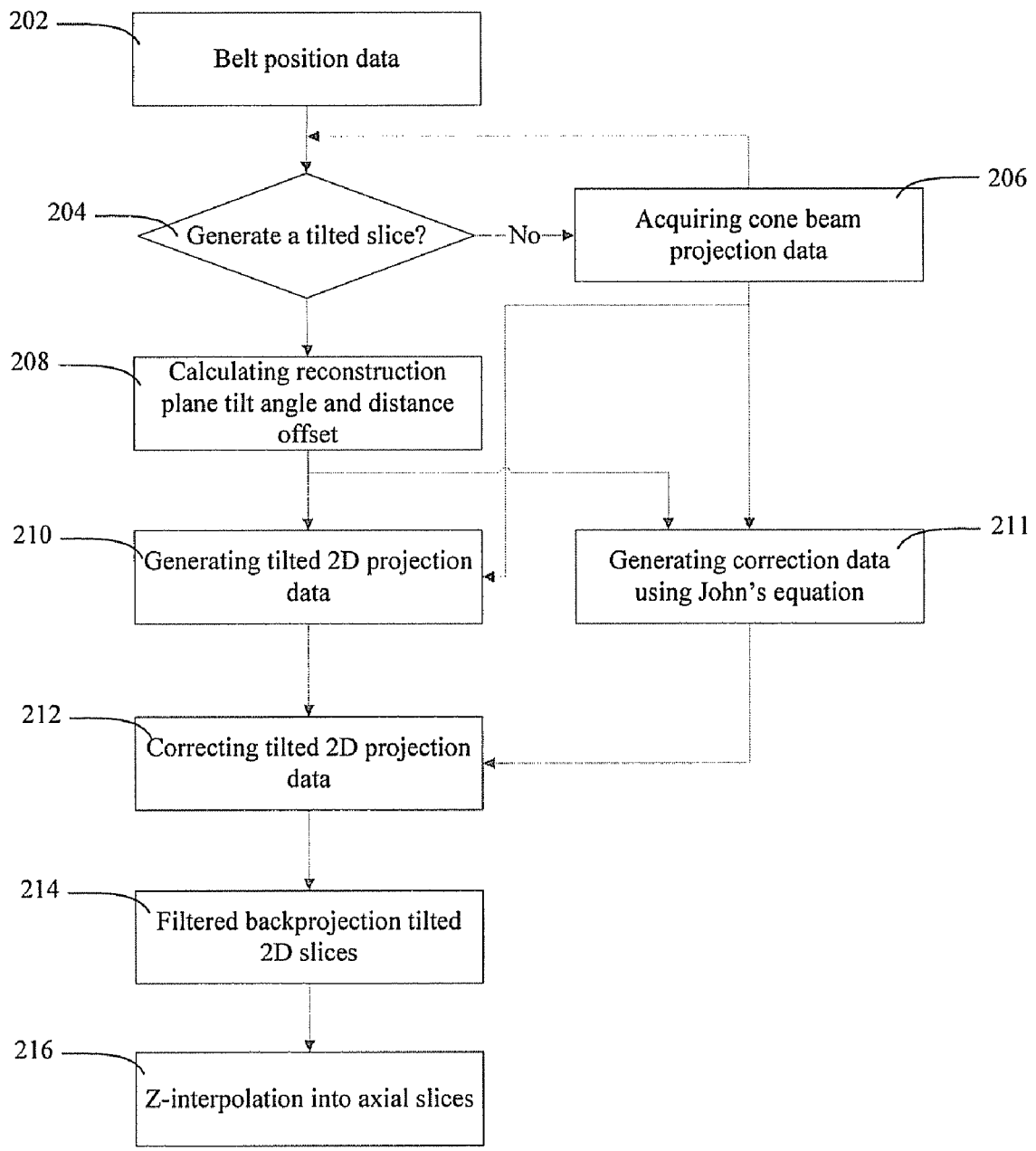
FIG. 6 is a block diagram which illustrates an example of an embodiment of the logical flow of the image reconstruction method of variable pitch scanning.
Figure 7A:
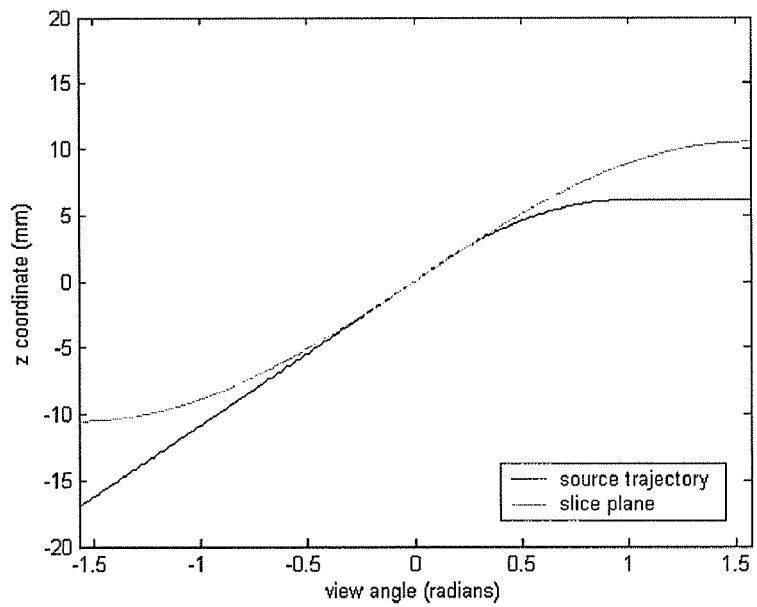
FIG. 7A is a plot of an example of the error between the x-ray source trajectory and the reconstruction plane with the optimization of the tilt angle only.
Figure 7B:
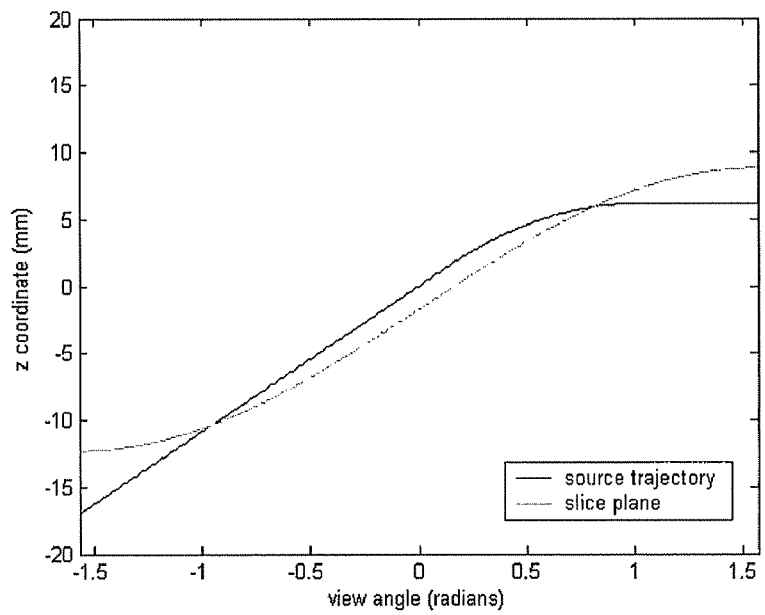
FIG. 7B is a plot of an example of the error between the x-ray source trajectory and the reconstruction plane with the optimization of the tilt angle and the distance offset.

FIG. 6 shows a block diagram of the logic flow of one embodiment of the image reconstruction method using variable pitch projection data. In Step 202, the conveyor belt position data is provided to the image reconstruction system. In Step 204, the following condition can be used for generating a new tilted slice:

$$b(t_{n+1}) - b(t_n) \geq d_z \qquad (1)$$

where $b(t_n)$ is the conveyor belt position at time $t_n$ of the $n^{th}$ tilted slice, $d_z$ is the desired slice spacing for the tilted slices, and usually is the detector pitch (the distance between the centers of two consecutive detectors) along the Z direction (the conveyor belt moving direction) at the isocenter (the center of the rotation) of the scanner. If the condition of Eq. (1) is not met, the image reconstruction system will wait until the belt moves to the desired position while the CT scanner continues to acquire projection data as shown in Step 206.

When the condition described in Eq. (1) is met, a tilted slice is reconstructed. A tilt angle, denoted by $\Phi(\alpha_c)$, for the reconstruction plane can be calculated as follows, $$\phi(\alpha_c) = -\tan^{-1} \frac{\alpha^* p(\alpha_c) w_{ziso} N_{rows}}{2\pi R_{sc} \sin \alpha^*} \qquad (2)$$

where $w_{ziso}$ is the detector pitch along the Z direction at the isocenter, $N_{rows}$ is the number of detector rows along the Z direction, $R_{sc}$ is the distance from the source to the isocenter, $\alpha_c$ is the projection angle corresponding to the center view of the projection data for reconstructing the tilted slice, $p(\alpha_c)$ is the helical scanning pitch at view angle $\alpha_c$, and $\alpha^*$ is a constant calculated as follows, $$\alpha^* = \cos^{-1} \frac{1}{2} \left( 1 + \cos \frac{\pi + \varphi_{os}}{2} \right)$$

where $\Phi_{os}$ is an over-scan angle and usually ranges from 10 to 20 degrees. The helical scanning pitch $p(\alpha_c)$ at view angle $\alpha_c$ can be calculated as follows, $$p(\alpha_c) = \frac{(b(t_v) - b(t_{v-1})) N_{vprot}}{w_{ziso} N_{rows}}$$

where $N_{vprot}$ is the number of sampling views (or projection angles) per rotation, $b(t_v)$ is the belt position at time $t_v$ corresponding to the center projection view angle $\alpha_c$, $b(t_{v-1})$ is the belt position at time $t_{v-1}$ corresponding to the projection view which is one view before the center projection view angle $\alpha_c$.

When a tilt angle and an offset of the reconstruction plane are both used for minimizing the error between the source trajectory and the reconstruction plane, the following procedures are used to generate the optimal tilt angle, denoted by $\Phi(\alpha_c)$, and the optimal offset for the tilted plane, denoted by $Z_0(\alpha_c)$, $$< \phi(\alpha_c),$$

$$Z_0(\alpha_c) >= \underset{\phi, Z_0}{\operatorname{argmin}} \int_{\alpha_c - \frac{\pi + \phi_{os}}{2}}^{\alpha_c + \frac{\pi + \phi_{os}}{2}} (R_{sc} \tan \phi \sin \alpha + Z_0 - w_{ziso} N_{rows} p(\alpha))^2 d\alpha$$

A brute force search can be employed, by way of example, to find the optimal pair of $\phi(\alpha_c)$ and $Z_0(\alpha_c)$. The tilt angle calculated in Eq. (2) and the offset distance $Z_0(\alpha_c) = 0$ are used as initial values for the search. The search is within predefined limits of both variables. Adding the distance offset can further minimize the error between the source trajectory and the reconstruction plane, therefore resulting in further improved image quality.

Referring to FIG. 6, a 2D fan beam projection data set corresponding to a tilted angle described in Eq. (2) is generated in Step 210 from the cone-beam data acquired in Step 206. The generation of the 2D fan beam projection data set typically comprises: A) computing the intersection line between the tilted reconstruction plane and the detector array; B) computing an index table and a weight table from the intersection line; and C) interpolating the cone-beam data using the computed index table and weight table to generate a 2D fan beam projection data set.

The intersection line between the tilted reconstruction plane and the detector array can be computed as follows, $$z'(v, s) = R_{sc}\sin\gamma(s)\cos\alpha_r(v)\tan\phi - \frac{p(a(v))N_{rows}w_{ziso}\alpha(v)}{2\pi}\cos\gamma(s) \quad (2A)$$

where z'(v,s) is the coordinate of the intersection line along the Z direction, v is the view index, s is the detector sample index along the fan direction, $\gamma(s)$ is the fan angle with respect to the line connecting the x-ray source and the isocenter, $\alpha_r(v)$ is the projection angle with respect to the center view angle $\alpha_c$, of the tilted slice to be reconstructed, and p(a(v)) is the helical scanning pitch at view angle $\alpha(v) = \alpha_c + \alpha_r(v)$.

The index table, denoted by I(v,s), can be computed as follows, $$I(v, s) = \begin{cases} 0, & r' < 0 \\ \lfloor r' \rfloor, & 0 \le r' \le N_{rows} - 2 \\ N_{rows} - 2, & r' > N_{rows} - 2 \end{cases}$$

where $$r' = \frac{z'(v, s)}{w_{ziso}} + \frac{N_{rows} - 1}{2}$$

and $\lfloor x \rfloor$ is the largest integer that is not greater than x.

The weight table, denoted by W(v,s), can be computed as follows, $$W(v, s) = \begin{cases} 0, & r' < 0 \\ r' - I(v, s), & 0 \le r' \le N_{rows} - 2 \\ 1, & r' > N_{rows} - 2 \end{cases}$$

Note that I(v,s) is the integer portion of the Z coordinate of the intersection line, and W(v,s) is the fraction portion of the Z coordinate of the intersection line. Therefore, the fan-beam projection data, denoted by $P_{fan}(v,s)$, corresponding to the tilted reconstruction plane can be obtained from the cone-beam projection data, denoted by $P_{cone}(v,s,r)$, as follows, $$P_{fan}(v,s) = P_{cone}(v,s,I(v,s))(1-W(v,s)) + P_{cone}(v,s,I(v,s)+1)W(v,s)$$

Due to the variable pitch, the error between the tilted reconstruction plane and the source helix is larger than at a constant pitch. Defrise et al. used John's equation to interpolate the projection data acquired at a constant pitch to correct the error between the source position and tilted reconstruction plane (M. Defrise, F. Noo, and H. Kudo, "Improved two-dimensional rebinning of helical cone-beam computerized tomography data using John's equation," *Inverse Problems*, vol. 19, pp. S41-S54, 2003).

Similarly, John's equation can be used to correct the error between the source trajectory and the tilted reconstruction plane at variable pitch helical scanning to reduce the cone-beam image artifacts. Referring to FIG. 6, correction data can be provided to compensate for the error between the source trajectory and the tilted reconstruction plane using John's equation at variable pitch helical scanning is generated at Step 211. The generation of the correction data using John's equation comprises the following steps: A) converting the cylindrical detector coordinates to flat panel detector coordinates; B) computing the axial deviation between the tilted reconstruction plane and the source trajectory; C) computing the John's approximation coefficient term; D) computing the derivatives of the projection data; and E) generating the correction data. The details of one embodiment of these steps are described below.

The flat panel detector coordinates, denoted by $(\mu,\upsilon)$, are calculated from the cylindrical coordinates (s,r) as follows, $$\mu(s) = -R_{sc}\tan\gamma(s), \quad \upsilon(r) = \left(r - \frac{N_{rows}-1}{2}\right)\frac{w_{ziso}}{\cos\gamma(s)}$$

The axial deviation between the tilted reconstruction plane and the source position, denoted by $C_1(\alpha((v)))$, is calculated as follows, $$C_1(\alpha(v)) = \frac{R_{sc}\tan\phi(\alpha_c)\sin\alpha_r(v) - (f(\alpha(v)) - f(\alpha_c))}{R_{sc}}$$

where $f(\alpha)$ is the source position along the Z axis, $$f(\alpha) = \int \frac{p(\alpha)}{2\pi} d\alpha$$

The John's approximation coefficient, denoted by $C_2(v,s,r)$, is calculated as follows, $$C_2(v, s, r) = \frac{R_{sc}\mu(s)\upsilon(r) - f_\alpha(\alpha(v))R_{sc}^2 + \upsilon(r)^2}{R_{sc}^2}$$

where $f_\alpha(\alpha)$ is the derivative of $f(\alpha)$, and is numerically calculated as follows, $$f_\alpha(\alpha(v)) = \frac{f(\alpha(v)) - f(\alpha(v-1))}{\alpha(v) - \alpha(v-1)}$$

The calculation of the second derivatives of the input projection data with respect to the projection angle and the detector column position is described below in detail. The input projection data, denoted by $P_{cone}(v,s,r)$ in cylindrical detector coordinates, and is denoted by $P(\alpha,\mu,\upsilon)$ in flat panel detector coordinates. The second derivatives needed for compensating the error include $P_{\upsilon\upsilon}(\alpha,\mu,\upsilon)$ and $P_{\alpha\upsilon}(\alpha,\mu,\upsilon)$. The Taylor's series expansion is used to compute these derivatives.

The projection data $P(\alpha,\mu,\upsilon_0)$ can be approximated using second order Taylor's expansion as follows, $$P(\alpha, \mu, \upsilon_0) = \quad (3A)$$
$$P(\alpha, \mu, \upsilon) + (\upsilon_0 - \upsilon)P_\upsilon(\alpha, \mu, \upsilon) + \frac{(\upsilon_0 - \upsilon)^2}{2}P_{\upsilon\upsilon}(\alpha, \mu, \upsilon)$$

Similarly, $P(\alpha,\mu,\upsilon_1)$ and $P(\alpha,\mu,\upsilon_2)$ can also be approximated as follows, $$P(\alpha, \mu, \upsilon_1) = P(\alpha, \mu, \upsilon) + (\upsilon_1 - \upsilon)P_\upsilon(\alpha, \mu, \upsilon) + \frac{(\upsilon_1 - \upsilon)^2}{2}P_{\upsilon\upsilon}(\alpha, \mu, \upsilon) \quad (3B)$$

$$P(\alpha, \mu, \upsilon_2) = P(\alpha, \mu, \upsilon) + (\upsilon_2 - \upsilon)P_\upsilon(\alpha, \mu, \upsilon) + \frac{(\upsilon_2 - \upsilon)^2}{2}P_{\upsilon\upsilon}(\alpha, \mu, \upsilon) \quad (3C)$$

Therefore, given three projection values, $P(\alpha,\mu,\upsilon_0)$, $P(\alpha,\mu,\upsilon_1)$, $P(\alpha,\mu,\upsilon_2)$, the projection value $P(\alpha,\mu,\upsilon)$, the first derivative $P_\upsilon(\alpha,\mu,\upsilon)$, and the second derivative $P_{\upsilon\upsilon}(\alpha,\mu,\upsilon)$, for $\upsilon_0 < \upsilon_1 < \upsilon_2$, can be obtained by solving the above three Eqs. (3A), (3B), and (3C).

The partial derivative $P_{\alpha\upsilon}(\alpha,\mu,\upsilon)$ can also obtained in a similar fashion as follows, $$P_\upsilon(\alpha_1,\mu,\upsilon) = P_\upsilon(\alpha,\mu,\upsilon) + (\alpha_1 - \alpha)P_{\alpha\upsilon}(\alpha,\mu,\upsilon) \quad (4A)$$

$$P_\upsilon(\alpha_2,\mu,\upsilon) = P_\upsilon(\alpha,\mu,\upsilon) + (\alpha_2 - \alpha)P_{\alpha\upsilon}(\alpha,\mu,\upsilon) \quad (4B)$$

Therefore, given two first derivatives of the projection values, $P_\upsilon(\alpha_1,\mu,\upsilon)$ and $P_\upsilon(\alpha_2,\mu,\upsilon)$ the partial derivative $P_{\alpha\upsilon}(\alpha,\mu,\upsilon)$, for $\alpha_1 < \alpha < \alpha_2$ can be obtained by solving the above two Eqs. (4A) and (4B).

The correction data, denoted by $P^J(\alpha,\mu)$, generated by John's equation is finally computed as follows, $$P^J(\alpha,\mu) = C_1(\alpha(\upsilon))(\Gamma_1 - \Gamma_2)$$

where $$\Gamma_1 = \frac{\mu_m - \mu}{2\mu_m} \sum_{i=1}^{N} (\mu(i+1) - \mu(i))[P_{\alpha\upsilon}(\alpha,\mu,\upsilon) - C_2(\upsilon,s,r)P_{\upsilon\upsilon}(\alpha,\mu,\upsilon)]$$

$$\Gamma_2 = \frac{\mu_m + \mu}{2\mu_m} \sum_{i=N+1}^{M} (\mu(i+1) - \mu(i))[P_{\alpha\upsilon}(\alpha,\mu,\upsilon) - C_2(\upsilon,s,r)P_{\upsilon\upsilon}(\alpha,\mu,\upsilon)]$$

where $\mu$ is at detector column position N, where there are total M columns of detectors, and $\upsilon$ is at the evaluated at the detector position according to Eq. (2A). The correction data $P^J(\alpha,\mu)$ in flat panel detector coordinates can be directly mapped back to $P^J(v,s)$ in cylindrical detector coordinates without additional calculation.

Referring to FIG. 6, in Step 212, the correction data $P^J(v,s)$ generated in Step 211 is added into the fan-beam data $P_{fan}(v,s)$ in Step 210 to produce the corrected fan-beam data, denoted by $P_{fan}^J(v,s)$, $$P_{fan}^J(v,s) = P_{fan}(v,s) + P^J(v,s)$$

In Step 214, the corrected fan-beam data then undergo a filtered back-projection operation to generate tilted slice images using, for example, the method described in "*Principles of Computerized Tomographic Imaging*," Avinash C. Kak and Malcolm Slaney, IEEE Press, 1988.

Referring to FIG. 6, in Step 216, tilted slices are interpolated along the Z axis on a pixel-by-pixel basis to form axial slices. Let $A_a[i,j,k]$ be the $k^{th}$ axial slice, and $A_t[i,j,l]$ be the $l^{th}$ tilted slice, the calculation of the $k^{th}$ axial slice is described below. Since the tilted slice is reconstructed at a constant interval at the isocenter along the Z axis, the axial slices are only formed at the same Z positions at the isocenter with the tilted slices; i.e. each axial slice intersects with one tilted slice. Assuming that the $k^{th}$ axial slice $A_a[i,j,k]$ intersects with the tilted slice $A_t[i,j,l_{cen}]$ at the isocenter, the calculation of the $k^{th}$ axial slice comprises: A) computing the Z distance between a set of tilted slices and the axial slice; B) computing weights for each pixel from two closest tilted slices, of which the axial pixel is in the middle; and C) interpolating the axial pixels using the pixels from the two closest tilted slices with the computed weights.

Assuming the maximal pitch of the scanner is known, the maximal tilt angle of the tilted slice, denoted by $\Phi_{max}$, is calculated according to the maximal pitch, thus the maximal number of tilted slices, denoted by $N_{tilt}$, to generate one axial slice is calculated as follows, $$N_{tilt} = 1 + \left\lceil \frac{2R_{fov}\tan\phi_{max}}{d_z} \right\rceil$$

where $R_{fov}$ is the radius of the reconstructed field of view, and $d_z$ is the slice spacing.

The distance between the tilted slice and the set of tilted slices with indices, $l_{cen} - (N_{tilt}-1)/2 \leq l < l_{cen} + (N_{tilt}-1)/2$ and the axial slice with index k is computed as follows, $$z[i,j,l] = [x[i]\cos\alpha(l) + y[j]\sin\alpha(l) + Z_0(\alpha(l))]\tan\Phi(l) + d_z(l - l_{cen})$$

where $d_z$ is the slice spacing, $\alpha(l)$ is the central view index and $\Phi(l)$ is the tilt angle of the reconstructed slice and $$x[i] = d_p\left(i - \frac{N_x - 1}{2}\right) + x_0$$

$$y[j] = -d_p\left(j - \frac{N_y - 1}{2}\right) + y_0$$

where $(x_0, y_0)$ is the image center with respect to the isocenter, and i,j are the pixel indices for each slice.

For each pixel (i,j), find the indices of the tilted slice, denoted by $l_{max}$ and $l_{min}$ that are closest to the axial slice, $$l_{max}[i,j] = \max_{z(i,j,l)<0} l, \quad l_{min}[i,j] = \min_{z(i,j,l)>0} l$$

The linear interpolation weight for each pixel is then computed as follows, $$w[i,j] = \frac{-z(i, j, l_{max}[i,j])}{z(i, j, l_{min}[i,j]+1) - z(i, j, l_{max}[i,j])}$$

The axial pixel $A_a[i,j,k]$ using the pixels from the two closest tilted slices with the computed weight is calculated as follows, $$A_a[i,j,k] = A_t[i,j,l_{max}[i,j]] + w[i,j](A_t[i,j,l_{min}[i,j]+1] - A_t[i,j,l_{max}[i,j]])$$

Note that the complexity of the above axial slice interpolation is reduced by storing the Z distance table for each rotation and for each discretized variable pitch within the range of the maximal pitch value.

While this disclosure has been particularly shown and described with references to preferred embodiments thereof, it will be understood by those skilled in the art that various changes in form and details may be made therein without departing from the spirit and scope of the disclosure as defined by the following claims.

The invention claimed is:

1. A method of image reconstruction using cone-beam projection data acquired at variable pitch by a detector array of a system including a movable conveyor belt positioned to move objects through a rotatable scanner gantry including the detector array, wherein the pitch is defined as the ratio of the conveyor belt displacement in one gantry rotation to the width of the detector array along the belt movement direction, the method comprising:
   A. Acquiring variable pitch cone-beam projection data;
   B. Computing a tilt angle and a distance offset for each tilted slice using the pitch values at which the cone-beam projection data is acquired for that tilted slice;
   C. Generating fan-beam projection data for each tilted slice using the tilted angle and the distance offset computed in Step B; and,
   D. Reconstructing tilted slices using the fan-beam projection data generated in Step C.

2. The method of claim 1, wherein the method further includes a step of interpolating the reconstructed tilted slices from Step D into axial slices.

3. The method of claim 1, wherein the system also includes a source for generating a cone-beam of X-rays along a source trajectory, and a tilted reconstruction plane is defined by the tilt angle and the distance offset, and Step C includes generating correction projection data to compensate for the error between the source trajectory and the tilted reconstruction plane.

4. A system for reconstructing images using cone-beam projection data acquired at variable pitch, the system comprising:
   A. A rotatable gantry including (1) a source for generating a cone-beam and (2) a detector array;
   B. A conveyor for moving objects through the rotatable gantry, wherein the system continue to obtain projection data for each slice with variations in the speed of the conveyor so as to define the variable pitch, the latter being defined as the ratio of the conveyor belt displacement in one gantry rotation to the width of the detector array along the belt movement direction; and
   C. A subsystem for dynamically calculating for each slice based on the belt speed or pitch the tilt angle and the distance offset of the reconstruction plane on which each slice is reconstructed.

5. A system according to claim 4, wherein the subsystem for dynamically calculating the tilt angle and the distance offset of the reconstruction plane is configured to calculate the tilt angle and the distance offset based on the minimization of the error between the source trajectory and the reconstruction plane of all the projection views of the slice.

6. A system according to claim 4, wherein the subsystem for dynamically calculating the tilt angle includes a low-pass filter configured to low-pass filter the tilt angles using several consecutive slices so as to reduce noise and outlier data points with regards to belt speed and belt position.

7. A system according to claim 4, wherein the subsystem for dynamically calculating the tilt angle and the distance offset is configured to calculate an intersection curve of the tilted reconstruction plane and the detector plane, and to generate fan-beam projection data for the tilted slice from the cone-beam projection data on the intersection curve.

8. A system according to claim 7, wherein the subsystem for dynamically calculating the tilt angle and the distance offset is further configured to use linear interpolation to generate the fan-beam projection data.

9. A system according to claim 4, wherein the subsystem for dynamically calculating the tilt angle and the distance offset is configured to generate correction projection data from cone-beam data acquired from a scan so as to compensate for errors between the x-ray source trajectory and the tilted reconstruction plane.

10. A system according to claim 9, wherein the subsystem is further configured to generate the correction projection data using second order derivatives with respect to the projection angle and the detector column direction, and to compute a summation of weighted second order derivatives.

11. A CT baggage scanner for screening bags, the scanner comprising:
   A. A rotatable gantry for scanning bags using cone-beam projections to generate slices; and
   B. A conveyor for transferring each bag through the gantry as the gantry rotates about the each bag; wherein the conveyor can decelerate when additional time is needed to render a decision on an undecided bag; accelerate to its normal speed when decisions are reached on undecided bags;
   wherein the system is configured to:
   i. generate cone-beam projection data at variable scanning pitch corresponding to variable conveyor speeds;
   ii. compute a tilt angle and a distance offset for each tilted slice using the pitch values at which the cone-beam projection data is acquired for that tilted slice;
   iii. generate fan-beam projection data for each tilted slice using the tilted angle and the distance offset;
   iv. generate correction projection data to compensate for the error between the x-ray source trajectory and the tilted reconstruction plane;
   v. generate the corrected fan-beam projection data by adding the correction projection data generated to the fan-beam projection data;
   vi. reconstruct tilted slices using the corrected fan-beam projection data; and
   vii. generate axial slices by interpolating the tilted slices.

* * * * *